United States Patent [19]

Warriner

[11] Patent Number: Plant 7,480

[45] Date of Patent: Mar. 26, 1991

[54] ROSE PLANT JACPIF

[75] Inventor: William A. Warriner, Tustin, Calif.

[73] Assignee: Bear Creek Gardens, Inc., Medford, Oreg.

[21] Appl. No.: 478,193

[22] Filed: Feb. 9, 1990

[51] Int. Cl.[5] ..... A01H 5/00

[52] U.S. Cl. ..... Plt./26

[58] Field of Search ..... Plt./26

*Primary Examiner*—James R. Feyrer

*Attorney, Agent, or Firm*—Klarquist, Sparkman, Campbell, Leigh & Whinston

[57] ABSTRACT

A Floribunda rose variety having a unique ruffled look to the petal edges, good tolerance to powdery mildew and rust, dark green leathery foliage, and a novel coral pink flower color.

1 Drawing Sheet

This present invention relates to a new and distinct variety of rose plant named JACPIF of the Floribunda class which was originated by me by crossing an unnamed seedling with the variety Intrigue, U.S. Plant Pat. No. 5,002.

The primary objective of this breeding was to produce a new rose variety having the plant habit of the parent Intrigue, coupled with the vigor and disease tolerance of the unnamed seedling parent. The objective was substantially achieved along with other desirable improvements as evidenced by the following unique combination of characteristics which are outstanding in the new variety and which distinguish it from its parents as well as from all other varieties of which I am aware:

1. A unique ruffled look to the petal edges.
2. Good tolerance to powdery mildew and rust.
3. Dark green leathery foliage.
4. Novel coral pink flower color.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated.

Parentage:

*Seed parent.*—An unnamed seedling.

*Pollen parent.*—Intrigue, U.S. Plant Pat. No. 5,002.

Clasification:

*Botanical.*—Rosa Hybrida.

*Commercial.*—Floribunda.

FLOWER

Observations made from specimens grown in a garden in Somis, Calif., from June to October, 1989.

Blooming habit. Recurrent.

Bud:

*Size.*—$\frac{3}{4}$ inch when the petals start to unfurl.

*Form.*—Long, pointed ovoid.

*Color.*—When sepals first divide: Red Group 52A to B. When half blown: The upper sides of the petals are Red Group 52C to D; and the lower sides of the petals are Red Group 52D.

*Sepals.*—Color: When recurved, Green Group 138C to D. Surfaced Texture: Covered in fine hairs. There are three normally appendaged sepals and two unappendaged sepals with hairy edges.

*Receptacle.*—Color: Green Group 138B. Shape: Funnel. Size: Small. Surface: Hairy with some glands.

*Peduncle.*—Length: Short. Surface: Prickly. Color: Light green. Strength: Stiff, erect.

Bloom:

*Size.*—Medium. Average open size is 3 to $3\frac{1}{2}$ inches.

*Borne.*—Several together, in flat clusters.

*Stems.*—Short, strong.

*Form.*—When first opened: High centered. Permanence: Flattens, outer petals curl back.

*Petalage.*—30–35.

*Color.*—The upper side of the petals is: Red Group 52C to D. The reverse side of the petals is: Red Group 52D. The base of the petals is: Small yellowish white half moon at the point of attachment. The major color on the upper side is: Red Group 52C to D.

*Variegations.*—None.

*Discoloration.*—General tonality at the end of the first day: None; at the end of the third day: None.

*Fragrance.*—Slight.

Petals:

*Texture.*—Thick.

*Shape.*—Round.

*Form.*—Tips slightly recurved.

*Arrangement.*—Imbricated. Petaloids in the center: Few.

*Persistence.*—Drop off cleanly.

*Lastingness.*—On the plant: Long. As a cut flower: Long.

Reproductive parts:

*Anthers.*—Size: Medium. Quantity: Many. Color: Reddish brown. Arrangement: Regular around styles.

*Filaments.*—Color: Yellow.

*Pollen.*—Color: Gold yellow.

*Styles.*—Color: Yellow.

*Stigmas.*—Color: Yellow.

Form: Bush.

Growth: Vigorous, upright, compact.

Foliage: Number of leaflets on normal mid-stem leaves: 5.

*Size.*—Large.

*Quantity.*—Normal.

*Color.*—New foliage: Bronze-red. Old foliage: Dark green.

Leaflets:

*Shape.*—Round, broadly oval.

*Texture.*—Leathery, semi-glossy.

*Edge.*—Serrated.

*Serration.*—Single, small.

*Petiole.*—Rachis: Green. Underside: Rough, with prickles.

*Stipules.*—Long to medium, serrated.

*Disease resistance.*—Resistant to powdery mildew and rust under normal growing conditions at Somis, Calif.

Wood:

*New wood.*—Color: Light green. Bark: Smooth.

*Old wood.*—Color: Green. Bark: Smooth, becoming rough at two (2) years of age.

Prickles:

*Quantity.*—On main canes from base: Ordinary. On laterals from main canes: Ordinary.

*Form.*—Hooked, slightly downward.

*Color when young.*—Red.

Small Prickles:

*Quantity.*—On main stalks: Few. On laterals: Few.

*Color.*—Brown.

I claim:

1. A new and distinct variety of rose plant of the Floribunda class, substantially as herein shown and described, characterized particularly as to novelty by the unique combination of its unique ruffled petals, upright vigourous habit of growth, good disease tolerance — especially to powdery mildew and rust, dark green leathery foliage and its unique coral pink flower color.

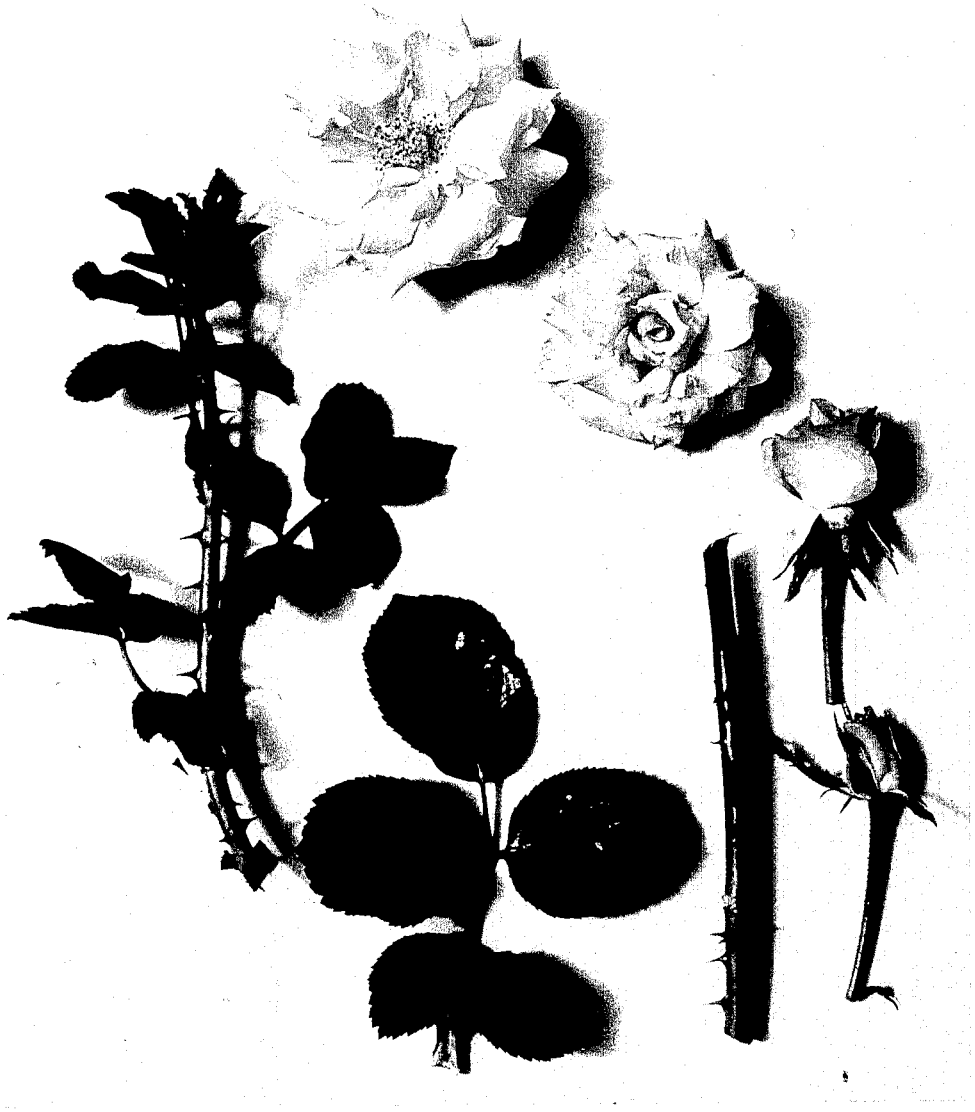

* * * * *